United States Patent [19]
Julius et al.

[11] Patent Number: 6,013,803
[45] Date of Patent: Jan. 11, 2000

[54] STERICALLY HINDERED 4-AMINO-PIPERIDINE WITH A LOW DIMER CONTENT, ITS PRODUCTION AND USE

[75] Inventors: Manfred Julius, Limburgerhof; Harald Rust, Neustadt; Alfred Krause; Hardo Siegel, both of Speyer; Wolfgang Siegel, Limburgerhof; Tom Witzel, Ludwigshafen, all of Germany

[73] Assignee: BASF Aktiengesellschaft, Ludwigshafen, Germany

[21] Appl. No.: 09/180,580

[22] PCT Filed: May 28, 1997

[86] PCT No.: PCT/EP97/02763

§ 371 Date: Nov. 12, 1998

§ 102(e) Date: Nov. 12, 1998

[87] PCT Pub. No.: WO97/46528

PCT Pub. Date: Dec. 11, 1997

[30] Foreign Application Priority Data

Jun. 3, 1996 [DE] Germany .................. 196 22 268

[51] Int. Cl.[7] .................. C07D 211/58; C07B 63/06
[52] U.S. Cl. .................. 546/187; 546/244
[58] Field of Search .................. 546/187, 244; 564/477, 503

[56] References Cited

U.S. PATENT DOCUMENTS

| | | | |
|---|---|---|---|
| 3,159,276 | 12/1964 | Moore | 564/477 |
| 3,207,790 | 9/1965 | Glew | 564/477 |
| 4,316,837 | 2/1982 | Molt et al. | 546/187 |

FOREIGN PATENT DOCUMENTS

| | | |
|---|---|---|
| 33 529 | 8/1981 | European Pat. Off. . |
| 477 593 | 4/1992 | European Pat. Off. . |
| 42 39 437 | 5/1994 | Germany . |
| 266 799 | 4/1989 | Netherlands . |

OTHER PUBLICATIONS

Manfred, J. "Preparation of 4–amino–2,2,6,6–tetramethylpiperidine (TAD) via . . . " 128:309121, 1997.
Controlling Colour Degradation . . . , Maffucci et al., Speciality Chem. 4 (2), pp. 38, 40, 41 (1984).

*Primary Examiner*—Ceila Chang
*Attorney, Agent, or Firm*—Keil & Weinkauf

[57] ABSTRACT

The invention relates to a process for reducing the dimerization of piperidines of the formula I

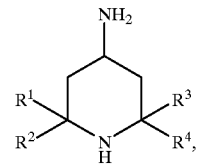

where $R^1$ to $R^4$ are $C_1$- to $C_6$-alkyl, $R^1$ and $R^2$ and/or $R^3$ and $R^4$ together are a $CH_2$ chain having 2 to 5 carbon atoms, which comprises adding to the piperidine from 0.001 to 0.2% by weight of a reducing agent of the formula $MXH_{4-m}Y_m$, where M is an alkali metal, $NR_4$, where R are identical or different $C_1$–$C_4$-alkyl groups, or an equivalent of an alkaline earth metal or an equivalent of zinc, X is boron or aluminum, Y is H or CN and m is 0 or 1. The invention also relates to a mixture of piperidines of the formula I, from 0.001 to 0.2% by weight of a reducing agent and from 1 to 1000 ppm of dimers of the piperidines of the formula I, and to the preparation of hindered amine light stabilizers therefrom.

7 Claims, No Drawings

STERICALLY HINDERED 4-AMINO-PIPERIDINE WITH A LOW DIMER CONTENT, ITS PRODUCTION AND USE

The present invention relates to a process for reducing the dimerization of piperidines of the formula I

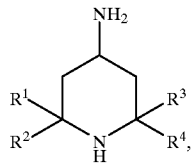

where $R^1$ to $R^4$ are $C_1$- to $C_6$-alkyl, $R^1$ and $R^2$ and/or $R^3$ and $R^4$ together are a $CH_2$ chain having 2 to 5 carbon atoms. The present invention furthermore relates to a mixture comprising piperidines of the formula I, from 1 to 1000 ppm of dimers of the formula II and from 0.001 to 0.2% by weight of a reducing agent, and to the use thereof for the preparation of HALS compounds.

Sterically hindered 4-aminopiperidines of the formula I are generally prepared on an industrial scale from acetone or acetone derivatives. I can be obtained in one step in a catalytic ring-closure reaction in the presence of ammonia and hydrogen from the compounds

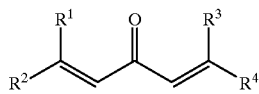

(DE 2 412 750) or from triacetoneamines of the formula III

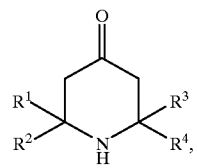

by reductive amination in one or two steps, for example catalytically (see, for example, DE 2 040 975, DE 2 349 962, DE 26 21 870, EP 33 529, EP 42 119, EP 303 279, EP 410 970, EP 611 137, EP 623 585 and DE 42 10 311). The sterically hindered 4-aminopiperidines prepared industrially are generally purified by distillation.

The sterically hindered 4-aminopiperidines of the formula I have a variety of applications. In particular, they are used as intermediates in the preparation of UV stabilizers for synthetic polymers. The present invention furthermore relates to a mixture comprising piperidine of the formula I, from 1 to 1000 ppm of a dimer of the formula II and from 0.001 to 0.2% by weight of a reducing agent, and to the use thereof for the preparation of HALS (hindered amine light stabilizer) compounds. These are usually piperidines of the formula I in which the nitrogen atom of the 4-amino group has been alkylated or acylated (see R. Gachter, H. Muller (editors), Taschenbuch der Kunststoff-additive, Carl Hanser Verlag, Munich, 1979; F. Gugumus, Polym. Degrad. Stabil. 44 (1994), 299–322).

For many applications, it is important that the piperidine of the formula I has high chemical purity. This is particularly true if the piperidine of the formula I is employed for the preparation of HALS compounds, since their product quality, and thus also the quality of the stabilized polymers, is crucially dependent on chemical purity. In particular, the dimer of the piperidine of the formula I, which is colorless, is an interfering by-product which forms in unacceptable amounts from the piperidine of the formula I even on storage under a protective gas in the dark at room temperature.

No processes are known for preventing dimerization of the piperidine.

U.S. Pat. No. 4,316,837 discloses the reduction of 4-aminopiperidyl groups in branched aliphatic alcohols to the corresponding 4-aminopiperidyl-containing branched alcohols. The dimer II of the piperidine I is not disclosed.

DD 266 799 describes purifying piperidines of the formula I by a process in which they are reacted in acetone/water solution with $CO_2$, the precipitate is separated off, washed with acetone and then pyrolyzed, and the product is purified by distillation. SU 18 11 527 describes another purification method for sterically hindered 4-aminopiperidines of the formula I, in which the unpurified crude product is dissolved in an aprotic solvent and reacted with ethylene glycol, and the reaction product is distilled and purified in a number of steps. Both processes are extremely complex and expensive. They do nothing to prevent the interfering subsequent formation of the dimer.

EP 477 593 discloses that the inherent color of crude N-alkyldialkanolamines can be improved by adding a metal borohydride and distilling the mixture under certain conditions in the presence of water. However, the N-alkyldialkanolamines are a completely different class of substances to the sterically hindered 4-aminopiperidines of the present invention. Furthermore, Spec. Chem. 4(2) (1984), 38–41, and U.S. Pat. No. 3,159,276, U.S. Pat. No. 3,207,790 and U.S. Pat. No. 3,222,310 disclose that the product color can be improved by addition of sodium borohydride to ethanolamines, ethyleneamines or aromatic amines. This publication likewise does not mention the piperidine of the formula I or a colorless dimer of the formula II.

It is an object of the present invention to prevent or suppress the dimerization of the piperidines of the formula I.

We have found that this object is achieved by the above-mentioned process, which comprises adding to the piperidine of the formula I from 0.001 to 0.2% by weight, based on the piperidine of the formula I, of a reducing agent of the formula $MXH_{4-m}Y_m$, where M is an alkali metal, $NR_4$, where R are identical or different $C_1$–$C_4$-alkyl groups, or an equivalent of an alkaline earth metal or an equivalent of zinc, X is boron or aluminum, Y is CN and m is 0 or 1. The invention also relates to the following mixture of substances: a piperidine of the formula I

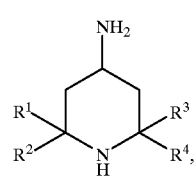

containing from 1 to 1000 ppm of a compound of the formula II

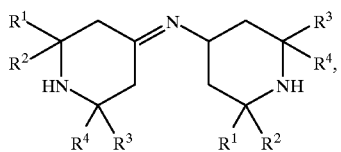

and from 0.001 to 0.2% by weight, in each case based on the piperidine of the formula I, of a reducing agent. The invention furthermore relates to the use of this mixture for the preparation of HALS compounds.

Further embodiments of the invention are given in the subclaims.

In the sterically hindered 4-aminopiperidines of the formula I, the radicals $R^1$, $R^2$, $R^3$ and $R^4$ are, independently of one another, preferably $C_1$- to $C_3$-alkyl, in particular ethyl or methyl, for example methyl.

The reducing agents employed are compounds of the formula $MXH_{4-m}Y_m$, where M is an alkali metal, $NR_4$, where R are identical or different $C_1$–$C_4$-alkyl groups, or an equivalent of an alkaline earth metal or an equivalent of zinc, preferably an alkali metal, in particular sodium or potassium, for example sodium, and X is aluminum or, in particular, boron, Y is CN and m is 1 or in particular 0. An example is sodium borohydride. In some cases, $(RaO)_2TiBH_4$ or $(RaO)_3TiBH_4$, where Ra is $C_1$–$C_4$-alkyl, have also proven successful.

The amount of reducing agent added to the piperidine of the formula I is preferably from 10 to 1000 ppm, in some cases up to 500 ppm, in particular up to 200 ppm, based on the piperidine of the formula I. In some cases, the reducing agent can also be added in amounts of greater than 50 ppm, in particular greater than 100 ppm, in each case based on the piperidine of the formula I.

The method by which it is added is unimportant. The reducing agent can be added in one or more portions to a vessel containing the piperidine of the formula I and mixed in, for example by stirring. This can be carried out batchwise or continuously, in the latter case for example also by metering the reducing agent into a product stream containing or consisting of the piperidine of the formula I. It is also in principle conceivable to interchange the initially charged and added substances. The temperature and pressure are unimportant, and the reducing agent can be added during the conventional steps in the preparation of the piperidine of the formula I, for example during or in particular after the distillation step for final purification of the piperidine of the formula I in the preparation process. The reducing agent can be added in powder form or as a solution, for example in pure piperidine of the formula I.

The substance mixture of claim 5 comprising piperidine of the formula I, dimer of the formula II and reducing agent can be prepared in a simple manner by first separating crude piperidine of the formula I from dimer of the formula II in the desired manner by distillation. This can be carried out, for example, by distillation since the dimer of the formula II has a significantly higher boiling point than the piperidine of the formula I. The person skilled in the art can easily determine the dimer content, for example by gas-chromatographic analysis. The reducing agent is then added as described.

HALS compounds are generally prepared from the novel mixture by alkylation or acylation of the piperidine of the formula I on the nitrogen atom of the 4-amino group in a conventional manner. The novel process provides a simple and inexpensive way of preparing pure, sterically hindered 4-aminopiperidines of the formula I which are virtually free from dimers. This stabilization can take place in a simple manner at room temperature and frequently gives easy-to-handle solutions which remain free from dimers for at least several weeks.

Advantageous HALS compounds having a reduced by-product content can be prepared therefrom.

EXAMPLES 4208 g of crude 4-amino-2,2,6,6-tetramethylpiperidine (triacetonediamine, TAD) having the composition 85.6% of triacetonediamine (TAD)

9.0% of $H_2O$ approx. 0.7% of low boilers 4.7% of medium and high boilers were rectified in a bench apparatus with a column containing 2.4 m of Sulzer CY packing (approximately 22 theoretical plates, nominal width 43 mm) at a reflux ratio of 5:1 and a pressure of from 100 to 40 mbar. After removal of the water in the first runnings at from 43 to 44° C. and 100 mbar, pure TAD fractions having a TAD content of >99.6% were obtained in the main runnings at 40 mbar and a head temperature of 97 to 103° C. (gas chromatography; 30 m capillary column RTX-5 amines); distillation yield: 3022 g (84%).

A pure TAD fraction (TAD content according to GC: 99.7%) was stored and measured under identical conditions firstly without addition of sodium borohydride and secondly with addition of 1000 ppm of sodium borohydride. The results are shown in the following table:

| Storage time in weeks | Composition according to GC (area %) | | | |
| --- | --- | --- | --- | --- |
| | Without addition of $NaBH_4$ | | With addition of $NaBH_4$ | |
| | TAD | Dimer II* | TAD | Dimer II* |
| 0 | 99.69 | 0.02 | 99.65 | 0.01 |
| 23 | 98.26 | 0.87 | 99.64 | 0.0001 to 0.001 |

*$R^1$, $R^2$, $R^3$ and $R^4$ = methyl

We claim:

1. A process for reducing the dimerization of piperidines of the formula I

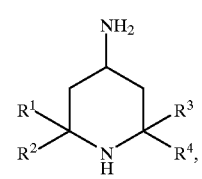

where $R^1$ to $R^4$ are $C_1$- to $C_6$-alkyl, $R^1$ and $R^2$ and/or $R^3$ and $R^4$ together are a $CH_2$ chain having 2 to 5 carbon atoms, which comprises adding to the piperidine from 0.001 to 0.2% by weight, based on the piperidine, of a reducing agent of the formula $MXH_{4-m}Y_m$, where M is an alkali metal, $NR_4$, where R are identical or different $C_1$–$C_4$-alkyl groups, or an equivalent of an alkaline earth metal or an equivalent of zinc, X is boron or aluminum, Y is CN and m is 0 or 1.

2. A process as claimed in claim 1, wherein $R^1$, $R^2$, $R^3$ and $R^4$ are $C_1$- to $C_3$-alkyl.

3. A process as claimed in claim 2, wherein the compound of the formula $MXH_{4-m}Y_m$ is sodium borohydride.

4. A mixture comprising

A. a piperidine of the formula I

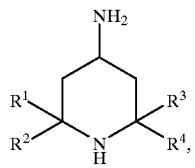

where $R^1$ to $R^4$ are $C_1$- to $C_6$-alkyl, $R^1$ and $R^2$ and/or $R^3$ and $R^4$ together are a $CH_2$ chain having 2 to 5 carbon atoms, B. from 1 to 1000 ppm, based on A, of a compound of the formula II

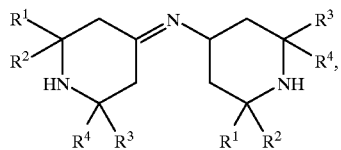

and

C. from 0.001 to 0.2% by weight, based on A, of a reducing agent of the formula $MXH_{4-m}Y_m$, where M is an alkali metal, $NR_4$, where R are identical or different $C_1$–$C_4$-alkyl groups, or an equivalent of an alkaline earth metal or an equivalent of zinc, X is boron or aluminum, Y is CN and m is 0 or 1.

5. A mixture as claimed in claim 4, where $R_1$, $R^2$, $R^3$ and $R^4$ are $C_1$- to $C_3$-alkyl.

6. A mixture as claimed in claim 4, where the compound of the formula $MXH_{4-m}Y_m$ is sodium borohydride.

7. A method of using a mixture as claimed in any of claim 4 for the preparation of HALS compounds.

* * * * *

UNITED STATES PATENT AND TRADEMARK OFFICE
CERTIFICATE OF CORRECTION

PATENT NO.: 6,013,803

DATED: January 11, 2000

INVENTOR(S): JULIUS et al.

It is certified that error appears in the above-identified patent and that said Letters Patent is hereby corrected as shown below:

Title page, item [57]
line 5 after the formula "$m\text{Y}_m$" should be --$_m\text{Y}_m$--.

Col. 6, claim 7, line 20, delete "any of".

Signed and Sealed this

First Day of August, 2000

Attest:

Q. TODD DICKINSON

*Attesting Officer*          *Director of Patents and Trademarks*